United States Patent
Stoddard (10) Patent No.: US 11,965,206 B2
(45) Date of Patent: Apr. 23, 2024

(54) METHOD OF DOSING A PATIENT WITH MULTIPLE DRUGS USING ADJUSTED PHENOTYPES OF CYP450 ENZYMES

(71) Applicant: John Stoddard, Brownsboro, AL (US)

(72) Inventor: John Stoddard, Brownsboro, AL (US)

(*) Notice: Subject to any disclaimer, the term of this patent is extended or adjusted under 35 U.S.C. 154(b) by 1356 days.

(21) Appl. No.: 16/228,840

(22) Filed: Dec. 21, 2018

(65) Prior Publication Data

US 2020/0199659 A1    Jun. 25, 2020

(51) Int. Cl.
*C12Q 1/6827*     (2018.01)
*G16B 20/00*     (2019.01)
*G16H 20/10*     (2018.01)
*G16H 50/20*     (2018.01)
*G16H 50/30*     (2018.01)

(52) U.S. Cl.
CPC ........... *C12Q 1/6827* (2013.01); *G16B 20/00* (2019.02); *G16H 20/10* (2018.01); *G16H 50/20* (2018.01); *G16H 50/30* (2018.01); *C12Q 2600/106* (2013.01); *C12Q 2600/142* (2013.01); *C12Q 2600/156* (2013.01)

(58) Field of Classification Search
CPC ...... C12Q 1/6827; G16H 50/30; G16H 50/20; G16H 20/10; G16B 20/00
See application file for complete search history.

(56) References Cited

U.S. PATENT DOCUMENTS

| | | |
|---|---|---|
| 8,099,298 B2 | 1/2012 | Coleman et al. |
| 8,401,801 B2 | 3/2013 | Mrazek et al. |
| 8,589,175 B2 | 11/2013 | Glauser et al. |
| 9,066,918 B2 | 6/2015 | Brown |
| 2003/0091975 A1 | 5/2003 | Leyland-Jones |
| 2006/0289019 A1 | 12/2006 | Marchand et al. |
| 2014/0024029 A1 | 1/2014 | Mrazek |
| 2014/0222400 A1 | 8/2014 | Coleman et al. |
| 2015/0174082 A1 | 6/2015 | Willmann et al. |
| 2016/0012181 A1 | 1/2016 | Massey et al. |
| 2016/0034667 A1 | 2/2016 | Rosenblatt et al. |
| 2017/0147779 A1 | 5/2017 | Glauser et al. |
| 2017/0199977 A1 | 7/2017 | Kane et al. |
| 2017/0270246 A1 | 9/2017 | Baskys |

OTHER PUBLICATIONS

Rebsamen et al. The AmpliChip CYP450 test: cytochrome P450 2D6 genotype assessment and phenotype prediction. The Pharmacogenomics Journal 2009, 9, pp. 34-41 (Year: 2009).*
Lynch et al. The Effect of Cytochrome P450 metabolism on Drug Response, Interactions, and Adverse Effects. American Family Physician 2007, vol. 76, No. 3, pp. 391-396 (Year: 2007).*
Rebsamen et al. The AmpliChip CYP450 test: cytochrome P450 2D6 genotype assessment and phenotype prediction. The Pharmacogenomics Journal 2009, vol. 9, pp. 34-41 (Year: 2009).*
Wilcox et al. An optimization-based approach to lookup table program transformations. Journal of Software: Evolution and Process 2014, vol. 26, pp. 533-551 (Year: 2014).*
Gardner, Donald, "Using Genomics to Help Predict Drug Interactions", Journal of Biomedical Informatics 37 (2004), pp. 139-146.
Low et al., "Drug-drug interactions involving antidepressants: focus on desvenlafaxine", Neuropsychiatric Disease and Treatment, (2018) 14; pp. 567-580.

* cited by examiner

*Primary Examiner* — Jerry Lin
(74) *Attorney, Agent, or Firm* — Gerald M. Walsh; Lanier Ford Shaver & Payne, PC (57) ABSTRACT

A method of treating a patient with multiple drugs using adjusted phenotypes of CYP450 enzymes to assess the risk of adverse drug reactions occurring due to drug-enzyme interactions. CYP450 enzyme genotypes and phenotypes are measured in a patient. The phenotypes are scored numerically. The drugs intended for treatment are scored numerically for their ability to induce or inhibit the CYP450 enzymes. The drug scores are used to adjust the CYP450 phenotype scores relative to inducing or inhibiting the enzymes. An accurate adjusted phenotype score for a given CYP450 enzyme is converted to an accurate adjusted phenotype. Any of the intended drugs for treatment that are substrates for the given CYP450 enzyme can be evaluated for risk of an adverse drug reaction based on the adjusted phenotype. This method of rapid risk assessment provides an accurate basis for decisions regarding changes in dose, eliminating a drug, or replacing a drug.

18 Claims, 3 Drawing Sheets

| Blood or saliva is obtained from a patient and analyzed for CYP450 enzyme genotypes. The genotype for each CYP450 enzyme is converted to a baseline standard phenotype which is used to designate a given subject's ability to metabolize drugs for a given CYP450 enzyme. |
|---|
| Step 1 |

↓

| A numerical score is provided for each baseline standard phenotype for the CYP450 enzymes wherein the phenotypes range from poor to intermediate to normal to rapid to ultra-rapid and wherein the scores increase in amount negatively (faster metabolism) from normal to ultra-rapid and increase in amount positively (slower metabolism) from normal to poor. |
|---|
| Step 2 |

↓

| For each drug to be administered to the patient the CYP450 enzymes are identified for which each drug is a substrate. Each drug is identified as to whether the drug is a strong, moderate, or weak inducer or a strong, moderate, or weak inhibitor of each of the CYP450 enzymes. |
|---|
| Step 3 |

↓

| For each drug that is an inducer a negative number is added, increasing in amount from a weak inducer to a strong inducer, to the baseline phenotype scores for the enzymes which are induced, to adjust the phenotype scores. |
|---|
| Step 4 |

↓

| For each drug that is an inhibitor a positive number is added, increasing in amount from a weak inhibitor to a strong inhibitor, to the baseline phenotype scores for the enzymes which are inhibited, to adjust the phenotype scores. |
|---|
| Step 5 |

METHOD OF DOSING A PATIENT WITH MULTIPLE DRUGS USING ADJUSTED PHENOTYPES OF CYP450 ENZYMES

FIELD OF THE INVENTION

The present invention relates to the use of drug metabolizing enzyme phenotypes for determining drug dosage and related risk factors and, more particularly, to providing a method of multiple drug dosing using adjusted drug metabolizing enzyme phenotypes to account for drug-enzyme interactions and to determine drug dosage. The adjusted phenotype identifies possible severe pathway interactions that can cause side effects and non-therapeutic response which may indicate a lower or higher dose or new medication.

BACKGROUND OF THE INVENTION

Many drugs are often prescribed based on the assumption that all patients respond to a drug in an identical or at least in a similar way. However, drug pharmacokinetic properties including absorption, distribution, metabolism and excretion vary markedly among individuals. Numerous genetic variants have been identified that influence not only drug metabolism but also drug efficacy by altering properties of the drug target as well as other aspects of drug actions. Recent advances in molecular genetics have provided methods for measuring the relationships between genetic variations, drug effectiveness and drug side effects which are referred to as pharmacogenetics. Pharmacogenetic testing has become commercially available for physicians who wish to prescribe or use medications taking into account a patient's genotypes for drug metabolizing enzymes.

Most commercially produced pharmacogenetic testing reports include data on approximately 15 to 130 pharmacogenes and they are impossible for a human mind to meaningfully integrate into a clinical decision during a short patient visit, which typically ranges from 7 to 15 minutes. A clinical pharmacist on average spends about 75 minutes with patients communicating pharmacogenetic results. The key measurements from pharmacogenetic testing are the genotypes of several enzymes, mainly in the liver, that metabolize drugs.

Drug metabolizing enzymes of the cytochrome P450 pathway (CYP450) metabolize more than 90% of available medications. The following enzymes are the most utilized CYP450 enzymes: 3A4, 3A5, 1A2, 2C9, 2B6, 2C19, 2C8 and 2D6. The genotype indicates the phenotype so that the genotype can be converted to a corresponding phenotype. The phenotype is a qualitative description of the relative rate of drug metabolism for a given CYP450 enzyme. Phenotypes are usually classified under five classes that determine the drug metabolism response rate to a number of medications: normal (extensive), intermediate (slow), poor (very slow), rapid (fast), and ultra-rapid (very fast).

Physicians use these phenotypes as a guide to dose a patient and/or to identify possible drug gene interactions that may be harmful. Drug doses recommended by a manufacturer are based on a normal phenotype in a normal patient population distribution. If a patient has an abnormal slow metabolizing enzyme for a given drug, such as intermediate, then the physician may have to adjust the recommended dose of the drug to a lower dose or choose an alternative medication without the genetic risk of impaired drug metabolism. If a patient has a fast metabolizing enzyme of a given drug, such as rapid, then the physician may want to adjust the recommended dose of the drug to a higher dose.

Dosing is further complicated by the fact that CYP450 enzymes can be altered by drugs that inhibit (slow down/block) drug metabolism or induce (speed up) drug metabolism. Thus, a physician must also consider the potential effects of one drug on another drug when determining dosage or drug interaction risk when a patient is receiving more than one drug. Aging and various disease states can increase or decrease drug metabolism and must also be considered in determining drug dosage and risk of adverse events due to genetic interactions.

Using pharmacogenetics to indicate doses of drugs or risk of genetic-based drug interactions for patients is known. U.S. Pat. No. 8,589,175 discloses using genotype and phenotype information to generate a dosage regimen for an individual patient. U.S. Patent Application No. 200160012181 discloses using genotype and phenotype information to recommend specific drugs for a patient. U.S Patent Application No. 20170270246 discloses using genotype and phenotype information to generate a graphical presentation to facilitate drug selection based on the totality of drug-gene and/or drug-drug interactions presented to the user as a visual graph. However, physicians know which drugs they would like to use and in which combinations. They rely on the phenotype of a patient for a given drug to make a quick decision as to dosage. In situations where two or more drugs are being administered to a patient the physician needs to know how the phenotype or phenotypical expression of each drug changes in the presence of another drug or other personal variables that can influence drug metabolic pathway expression. What is needed but heretofore has not been available is a method of administering two or more drugs to a patient based upon adjusted phenotypes (phenotypical expression) for each drug wherein the adjusted phenotypes accurately reflect the true phenotypes or genetic expression of the patient for a given drug or drugs sharing same drug metabolic pathway risk in the presence of other drugs. Adjusted phenotypes would allow a physician to assess risk of adverse drug reactions quickly and accurately in a patient receiving multiple drugs, in the same way the physician would when assessing risks in a patient receiving a single drug.

SUMMARY OF THE INVENTION

The present invention provides a method of treating a patient with multiple drugs using adjusted phenotypes of drug metabolizing enzymes which are altered in metabolic rate by one or more of the multiple drugs. A person, such as a physician or nurse, obtains tissue or fluid from a patient and has the tissue or fluid analyzed for CYP450 enzyme genotypes by standard pharmacogenetic methods. The CYP450 enzyme genotypes are converted to standard baseline phenotypes used to designate a given patients ability to metabolize drugs for each CYP450 enzyme. A numerical score is provided for each standard baseline phenotype based on degree of drug metabolism. Each of the multiple drugs is identified as to whether the drug is an inducer or inhibitor of each of the CYP450 enzymes. For each drug that is an inducer, the standard baseline phenotype scores are adjusted for the CYP450 enzymes which are induced, to indicate increased drug metabolism and for each drug that is an inhibitor, the baseline standard phenotype scores adjusted for the CYP450 enzymes which are inhibited, to indicate decreased drug metabolism, thereby obtaining a total adjusted phenotype score for each of the CYP450 enzymes which are induced or inhibited.

The adjusted phenotype scores are converted to adjusted phenotypes for the CYP450 enzymes which are induced or inhibited. Each of the multiple drugs that is a substrate for each CYP450 enzyme that has an adjusted phenotype is identified. The risk of an occurrence of adverse events with the use of each of these drugs is determined based upon the adjusted phenotype of each CYP450 enzyme for which each of the these drugs is a substrate. The dose of each of these drugs identified as a substrate is adjusted based on the determination of the risk. The patient is then treated with each of these drugs using the adjusted dose, if the risk of each is acceptable.

The standard baseline phenotypes range from poor to intermediate to normal to rapid to ultrarapid. The standard baseline phenotype scores increase in amount negatively from normal to ultrarapid and increase in amount positively from normal to poor. Each of the multiple drugs is identified as a strong, medium, or weak inducer or a strong, moderate, or weak inhibitor of each of the CYP450 enzymes. For each drug that is an inducer a negative number, increasing in amount from a weak inducer to a strong inducer, is added to the standard baseline phenotype scores for the CYP450 enzymes which are induced by each drug. For each drug that is an inhibitor a positive number, increasing in amount from a weak inhibitor to a strong inhibitor, is added to the standard baseline phenotype scores for the CYP450 enzymes which are inhibited by each drug.

A positive number adjustment may be added to a standard baseline phenotype score if a patient is 65 years of age or older. With dosages greater than 115% of average starting dose, per drug label, the standard baseline phenotype score may be adjusted by adding a positive number. With dosages less than 85% of average daily dose, per drug label, the standard baseline phenotype score may be adjusted by adding a negative number. All access to drug information data bases and all calculations of adjusted phenotypes can be performed automatically in a programmed computer.

An advantage of the present invention is a method which allows accurate rapid risk assessment of adverse drug reactions that may occur with multiple drug dosing.

Another advantage is a method which provides CYP450 enzyme phenotypes which are accurately adjusted to correct for any drug interactions on the CYP450 enzymes so that the adjusted phenotypes may be used for risk assessment of adverse drug reactions occurring in multiple drug dosing.

Another advantage is a method which allows accurate rapid drug interaction risk assessment so that drug dosage may be adjusted, or drugs may be deleted or replaced in multiple drug dosing.

Another advantage is the ability to make phenotype adjustments based upon highly reliable drug information in historical records, databases, and publications electronically.

Another advantage is a method of adjusting CYP450 enzyme phenotypes using a computer implemented software program so that all that is required is data entry into the computer program of the drugs to be used and the CYP450 enzyme genotypes of the patient, wherein the computer program can the provide the adjusted phenotype within ten minutes.

DETAILED DESCRIPTION OF THE INVENTION

While the following description details the preferred embodiments of the present invention, it is to be understood that the invention is not limited in its application to the details of method illustrated in the accompanying figure and tables, since the invention is capable of other embodiments and of being practiced in various ways.

In the treatment of a patient with several drugs at one time, side effects and toxicity can occur in the patient as a result of one or more of the drugs reducing or inhibiting metabolism of another of the drugs. On the other hand, one or more of the drugs may induce or accelerate metabolism of another of the drugs so that the drugs may not exert its therapeutic effect. The drug metabolizing enzyme phenotypes of a patient can be measured and can be categorized as to the rate of metabolism of drugs as extensive, slow, very slow, fast, or very fast. A physician uses these patient phenotype categories to estimate the risk of an adverse or unwanted effect of the drug occurring. Based on the patient's phenotypes for drug metabolizing enzymes and on the information supplied by the drug manufacturer as to which drug enzymes metabolize a specific drug, the physician can increase or decrease the recommended dose of a drug or choose an alternative drug without the associated risk of adverse events. This approach of adjusting the dose of the drug is effective in preventing an adverse drug reaction. However, when several drugs are administered at one time to a patient the drug metabolizing enzyme phenotypes may be altered or express a different phenotype than innate phenotype, and the physician can no longer rely on the measured drug metabolizing enzyme phenotypes of the patient to estimate a proper dosage. The present invention solves this problem by providing an estimation method of adjusting the drug metabolizing enzyme phenotypes (current expression) based upon what is known about the pharmacogenetic effects of drugs on drug metabolizing enzymes (Pharmacokinetics). The physician can rely on the adjusted phenotypes (current expression) to assess risk of adverse drug reactions and to adjust dosage quickly.

Table 1 lists the standard phenotypes assigned to a given CYP450 enzyme. Numeric values are assigned to each phenotype. The values increase in amount negatively going from normal to ultra-rapid. The values increase in amount positively going from normal to poor. The process of aging can decrease drug metabolizing (hepatic) activity, so the score (expression) can be adjusted by adding the appropriate age factor amount to the score. For example, a person with an intermediate phenotype of a given CYP450 enzyme would have a score of 0.35 for that enzyme. If that person was 70 years old the score should be corrected by adding 0.05 to the score to give a score of 0.40, thereby factoring the increased risk of decreased genetic drug metabolic enzyme expression due to age and decrease in liver function as one ages.

TABLE 1

Assigning a Score to Standard CYP450 Enzyme Phenotypes

|  |  | Age Factor | | |
|---|---|---|---|---|
| Phenotype | Score | Low | High | Factor |
| UltraRapid | −0.70 | 0 | 65 | 0.00 |
| Rapid | −0.40 | 65 | 75 | 0.05 |
| Normal | 0.00 | 75 | 120 | 0.10 |
| Intermediate | 0.35 | | | |
| Poor | 0.70 | | | |

Table 2 lists adjustments to the phenotype score for any drug that induces drug enzyme metabolizing activity for a given CYP450 enzyme. A drug that is an inducer of one or more CYP450 enzymes is characterized as a strong, moderate, or weak inducer of the enzyme. Strong, moderate, and weak are scored in increasing negativity from weak to strong. If there are more drugs that are inducers being given to the patient then the degree of negativity is increased for each category of weak, moderate, or strong for each additional drug that is an inducer. For example, if there are five drugs being given to a patient that are all weak inducers of the same CYP450 enzyme, then the score for that enzyme is adjusted by adding −0.90, based on Table 2.

TABLE 2

Adjustment to Phenotype Based on Degree of Enzyme Induction by a Drug

| | Inducer Factor | | |
|---|---|---|---|
| Drug # | Strong | Mod | Weak |
| 0 | 0.00 | 0.00 | 0.00 |
| 1 | −0.25 | −0.16 | −0.10 |
| 2 | −0.58 | −0.38 | −0.20 |
| 3 | −0.90 | −0.60 | −0.30 |
| 4 | | −0.90 | −0.67 |
| 5 | | | −0.90 |

Table 3 lists adjustments to the phenotype score for any drug that inhibits drug enzyme metabolizing activity for a given CYP450 enzyme. Certain CYP 450 enzymes are less or more susceptible to inhibition based on a size of pathway. 3A4, 2C9 and 1A2 have many more enzymes available for a drug, whereas 2C19, 2B6 and 2D6 have fewer enzymatic sites and are impacted greater by inhibition. This is reflected in Table 3 and explains why each CYP450 enzyme has it's own table for inhibition and induction effect. A drug that is an inhibitor of one or more CYP450 enzymes is characterized as a strong, moderate, or weak inhibitor of the enzyme. Strong, moderate, and weak are scored in increasing positivity from weak to strong. If there are more drugs that are inhibitors being given to the patient then the degree of positivity is increased for each category of weak, moderate, or strong for each additional drug that is an inducer. For example, if there are three drugs being given to a patient that are all moderate inhibitors of the same CYP450 enzyme, then the score for that CYP450 enzyme is adjusted by adding 0.65, based on Table 3.

TABLE 3

Adjustment to Phenotype Based on Degree of Enzyme inhibition by a Drug

| | Inhibitor Factor | | |
|---|---|---|---|
| Drug # | Strong | Mod | Weak |
| 0 | 0.00 | 0.00 | 0.00 |
| 1 | 0.37 | 0.20 | 0.10 |
| 2 | 0.63 | 0.41 | 0.22 |
| 3 | 1.00 | 0.65 | 0.40 |
| 4 | | 1.00 | 0.67 |
| 6 | | | 1.00 |

Each drug may interact with more than one CYP450 drug metabolizing enzyme. A drug may be a substrate for one CYP450 enzyme, an inducer of another CYP450 enzyme, and an inhibitor of yet another CYP450. One can understand that administering four or five drugs to a patient would involve complex calculations that are not feasible to perform in a clinical situation in which a physician wishes to adjust doses to avoid serious adverse drug reactions. The physician cannot rely on the standard CYP450 phenotypes for the various CYP450 enzymes involved because the CYP450 phenotypes may all be altered and expressed differently from normal by the combination of the drugs. The present invention provides a practical and useful way to overcome this problem.

Once the scores for the CYP-450 drug metabolizing enzymes have been adjusted as described above and a new score for each CYP-450 drug metabolizing enzyme has been calculated, then the score is converted to a new phenotype, i.e., and adjusted phenotype. Table 4 provides a look up table as an example of a way to look up an adjusted phenotype from an adjusted score. Preferably, the phenotype categories are expanded to provide more precision in the estimate of phenotype and to expand the range of risk associated with the phenotypes. Between the poor and intermediate categories is intermediate-poor. Between intermediate and normal is normal-intermediate. Between normal and rapid is rapid-normal. Between rapid and ultrarapid is ultrarapid-rapid. Instead of a single score being given for each phenotype designation, a range of scores is given. Once an adjusted phenotype score is obtained, a table of values such as those shown in Table 4 can be used to convert the adjusted phenotype score to an adjusted phenotype. Thus, if a specific CYP450 enzyme had an adjusted phenotype score of 0.61, then the adjusted phenotype for that CYP450 enzyme would be intermediate-poor. Any of the drugs that are metabolized by that enzyme might have a risk of increased adverse events. A provider can quickly identify the drugs affecting the CYP450 pathway expression and increasing the risk of adverse events; just as the provider can in the case where only a single drug is administered.

TABLE 4

Adjusted Phenotype Lookup

| Adjusted Phenotype | Low | High |
|---|---|---|
| UltraRapid | −10.00 | −0.65 |
| UltraRapid-Rapid | −0.64 | −0.52 |
| Rapid | −0.51 | −0.33 |
| Rapid-Normal | −0.32 | −0.16 |
| Normal | −0.15 | 0.15 |
| Normal-Intermediate | 0.16 | 0.36 |
| Intermediate | 0.37 | 0.51 |

TABLE 4-continued

Adjusted Phenotype Lookup

| Adjusted Phenotype | Low | High |
|---|---|---|
| Intermediate-Poor | 0.52 | 0.69 |
| Poor | 0.70 | 10.00 |

Figure 1A:
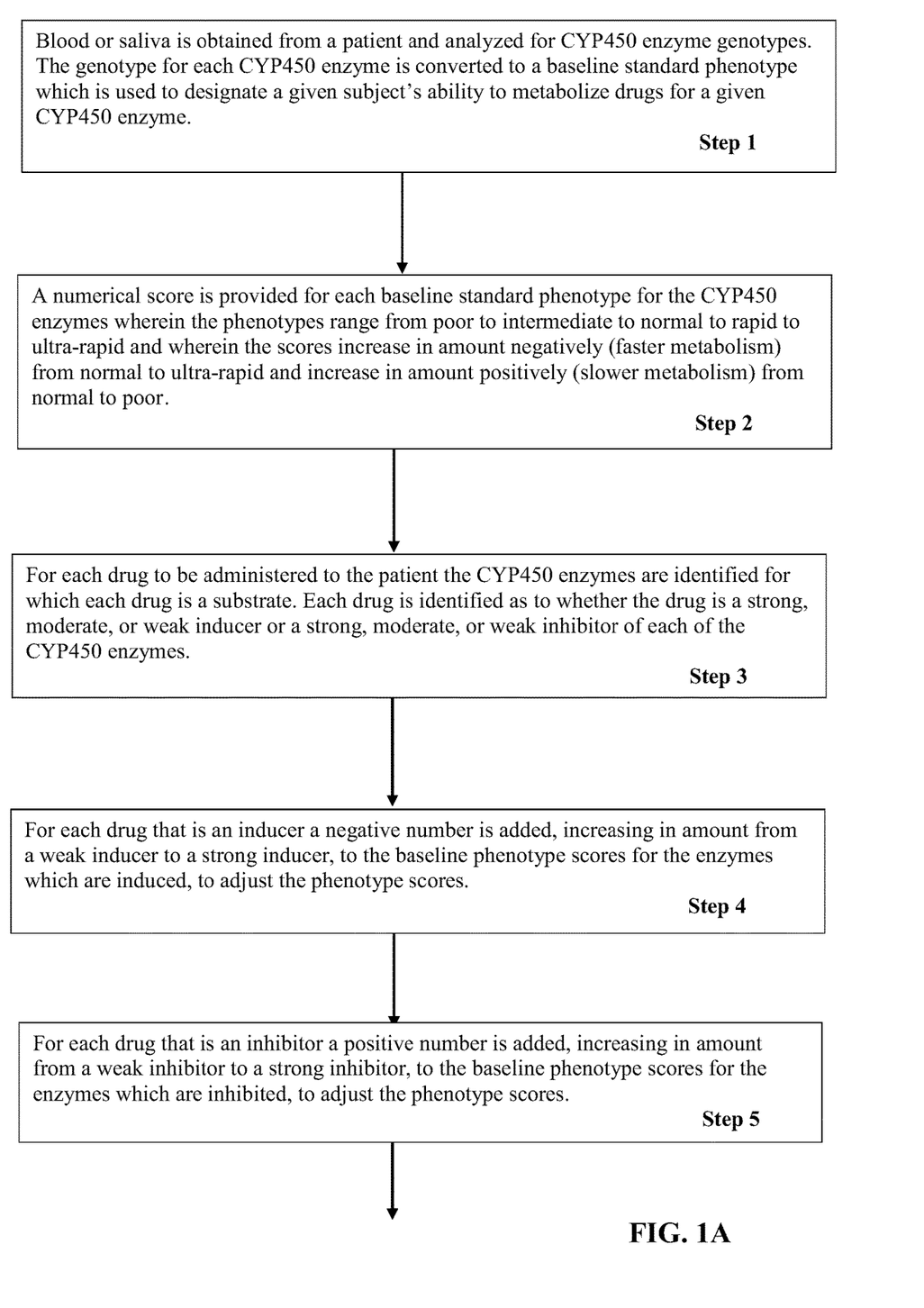
FIG. 1 is flow chart describing the steps of the method of the present invention of obtaining adjusted phenotypes of CYP450 drug metabolizing enzymes for risk assessment of adverse drug reactions in multidrug dosing in patients.
Figure 1B:
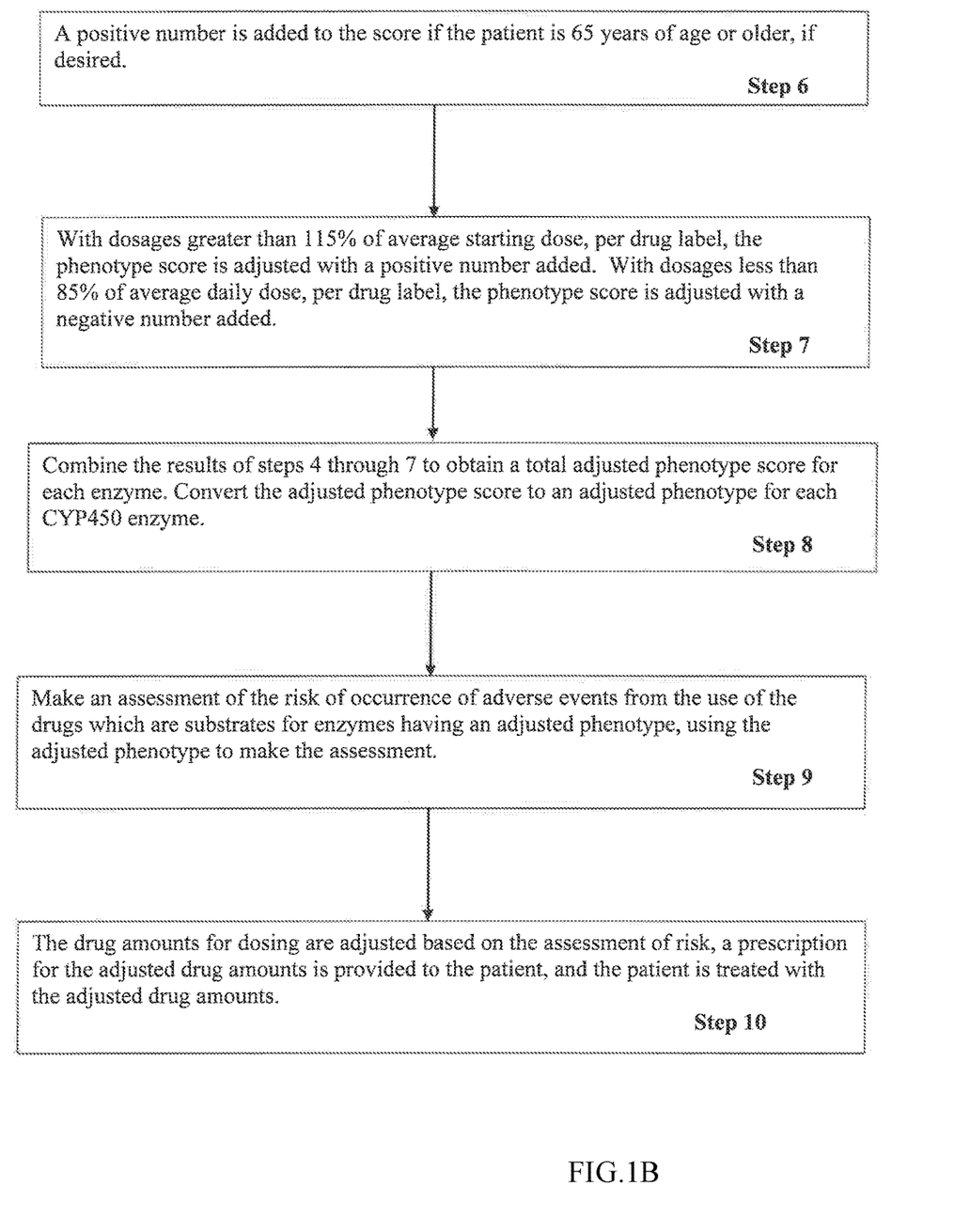

FIG. 1 illustrates the steps of the method of the present invention for treating a subject with multiple drugs. Blood or saliva is obtained from a subject and analyzed for CYP450 enzyme genotypes by methods well known in the art. The enzymes are, preferably, 3A4, 3A5, 1A2, 2C9, 2B6, 2C19, 2C8 and 2D6. The genotype for each CYP450 enzyme is converted to a baseline standard phenotype which is used to designate a given subject's ability to metabolize drugs for a given CYP450 enzyme, as is known in the art (Step 1). A numerical score is provided for each baseline standard phenotype for CYP450 enzymes wherein the phenotypes range from poor to intermediate to normal to rapid to ultra-rapid and wherein the scores increase in amount negatively (faster metabolism) from normal to ultra-rapid and increase in amount positively (slower metabolism) from normal to poor (Step 2).

For each drug to be administered to the patient the CYP450 enzymes are identified for which each drug is a substrate. Each drug is identified as to whether the drug is a strong, moderate, or weak inducer or a strong, moderate, or weak inhibitor of each of the CYP450 enzymes (Step 3). For each drug that is an inducer a negative number is added, increasing in amount from a weak inducer to a strong inducer, to the baseline phenotype scores for the enzymes which are induced, to adjust the phenotype scores (Step 4). For each drug that is an inhibitor a positive number is added, increasing in amount from a weak inhibitor to a strong inhibitor, to the baseline phenotype scores for the enzymes which are inhibited, to adjust the phenotype scores (Step 5). Patient age is identified, and a positive number is added to the phenotype score if, for example, the patient is 65 years of age or older Step 6).

With dosages greater than 115% of average starting dose per drug label the phenotype score is adjusted with positive number added. With dosages less than 85% of average daily dose per drug label the phenotype score is adjusted with a negative number added (Step 7). These dose related adjustments are based on clinical findings that inhibition, induction and substrate risk are increased or decreased based on the amount of drug ingredient prescribed. In other words, a drug that is a weak inhibitor of CYP pathway A in larger dosages than normal will inhibit at a greater strength than at a weaker strength and further adjust phenotypical expression to the slower (more positive score) phenotype while increasing the risk of needing a dose adjustment (an increased dose).

The results of steps 4 through 7 are combined to provide a total adjusted phenotype score. The total adjusted phenotype score is converted to an adjusted phenotype using, for example, a table such as Table 4 (Step 8). The risk of occurrence of adverse events from the use of the drugs which are substrates for enzymes having an adjusted phenotype are assessed, using the adjusted phenotype to make the assessment (Step 9). The drug amounts for dosing can adjusted based on the adjusted phenotypes, a prescription for the adjusted drug amounts can provided to the patient, and the patient can be treated with the adjusted drug amounts (Step 10).

This method of adjusting patient phenotypes of CYP450 drug metabolizing enzymes can be implemented in a computer or processor using standard software programs and algorithms. Such software programs implementing this method can be sold and/or licensed to drug prescribers, related personnel, and the like (users) for a fee. Alternatively, a user can access a website of a provider of this method and can, for a fee, access a program that will allow the user to input information such as patient age, drugs being prescribed, and the genotypes of the CYP450 enzymes for that patient.

Example 1

A patient age 68 is to receive metoprolol, paroxetine, diltiazem, Irbesartan, and glyburide. The patient's physician obtains a sample of blood or saliva from the patient and obtains a pharmacogenetic analysis of the patient's genotype for CYP450 enzymes 2D6, 2C9, 3A4, and 2C19. Based on the genotype results the phenotypes for the enzymes were 2D6=normal; 2C9=intermediate; 3A4=normal; and 2C19=normal. The user enters the patients age, drugs to be prescribed, and the enzyme phenotypes into a program that performs steps of the present invention. The program calculates a starting (baseline) phenotype score, adds a correction for age, searches one or more drug databases and finds that metoprolol is a substrate for 2D6, paroxetine is a substrate for 2D6 and strong inhibitor of 2D6, Diltiazem is a substrate for 3A4 and a weak inhibitor of 2D6, Irbesartan is a substrate for 2C9, and glyburide is a substrate for 2C9. Scoring and calculations are made as follows, as described for Tables 1-4:

| | | | Scores | | | | |
|---|---|---|---|---|---|---|---|
| Enzyme | Baseline Phenotype | Baseline Score | Age | Inducer | Inhibitor | Total score | Adjusted Phenotype based on total score |
| 2D6 | normal | 0 | 0.05 | 0 | 0.37 + 0.1 | 0.52 | intermediate poor |
| 2C9 | intermediate | 0.35 | 0.05 | 0 | 0 | 0.40 | intermediate |
| 3A4 | normal | 0 | 0.05 | 0 | 0 | 0.05 | normal |
| 2C19 | normal | 0 | 0.05 | 0 | 0 | 0.05 | normal |

The phenotype for the 2D6 enzyme is adjusted from normal to intermediate poor. The other phenotypes are not altered. A user can readily see that there is a significant risk with the drugs that are substrates for the 2D6 enzyme which are metoprolol and paroxetine. With the drug combination in this example metoprolol and paroxetine may be metabolized to a lesser degree than normal. The result could be toxicity related to abnormally high blood levels of these drugs. The adjusted phenotypes produced by the method of this invention provide reliable phenotypes for a user to make decisions on drug dosage, such as making changes in dose or making substitutions of the drugs.

Example 2

A patient age 46 is to receive Depakote, Prozac, Zyprexa, Abilify, Haldol, Benadryl, Lexapro and Risperdal. Pharmacogenetics testing revealed the following phenotypes for the CYP450 enzymes: 2B6=intermediate, 2C19=ultrarapid, 2D6=poor; 3A5=poor; 2C9=normal; and 3A4=normal. The user enters the patient's age, drugs to be prescribed, and the enzyme phenotypes into a computer program that performs steps of the present invention. The program calculates a starting (baseline) phenotype score and searches one or more drug databases and finds that Depakote is a substrate for 2C9 and 2B6, Prozac is a substrate for 2C9 and 2D6, Zyprexa is a substrate for 1A2 and 2D6, Abilify is a substrate for 2D6 and 3A4, Haldol is a substrate for 2D6 and 3A4, Benadryl is a substrate for 2D6, Lexapro is a substrate for 2C19 and 3A4; and Risperidone is a substrate 2D6 and 3A4. The search further finds that Depakote is a weak inhibitor of 2C9, 2C19 and 3A4, Prozac is a moderate inhibitor of 2C9 and 2C19, a strong inhibitor of 2D6, and a weak inhibitor of 3A4, Haldol is a weak inhibitor of 2D6; Benadryl is a weak inhibitor of 2D6; Lexapro is a weak inhibitor of 2D6; and risperidone is a weak inhibitor of 2D6. Scoring and calculations are made as follows, as described for Tables 1-4:

| | | Scores | | | | |
|---|---|---|---|---|---|---|
| | Baseline | Baseline | Inhibitor | | | Total Adjusted Phenotype |
| Enzyme | Phenotype | Score | weak | moderate | strong | score based on total score |
| 2B6 | intermediate | 0.35 | 0 | 0 | 0 | 0.35 intermediate |
| 2C19 | ultrarapid | −0.70 | 0.10 | 0.20 | 0 | −0.4 rapid |
| 2D6 | poor | 0.70 | 0.67 for 4 | 0 | 0.37 | 1.74 poor |
| 3A5 | poor | 0.70 | 0 | 0 | 0 | 0.70 poor |
| 2C9 | normal | 0.00 | 0.10 | 0.2 | 0 | 0.30 normal-intermediate |
| 3A4 | normal | 0.00 | 0.22 for 2 | 0 | 0 | 0.22 normal-intermediate |

The phenotypes for 2C9, 3A4, and 2C19 were adjusted. Depakote and Prozac are substrates for 2C9. The adjustment from normal to normal-intermediate for 2C9 would indicate an increased risk of side effects with Depacote and further increased risk of adverse events with Prozac. Abilify, Haldol, and Resperdal are substrates for 3A4. The adjustment of 3A4 from normal to normal-intermediate would indicate an increased risk of adverse events with these drugs. Lexapro is a substrate for 2C19 and 3A4. The adjustment of 2C19 from ultrarapid to rapid and 3A4 from normal to normal-intermediate would indicate that Lexapro may not be metabolized as it would be in the absence of the other drugs but the adjusted phenotype for 2C19 to only rapid would suggest a risk still of under dosing with Lexapro and not achieving a therapeutic response. With regard to 2D6, even if the patient had a normal phenotype for 2D6, the four weak inhibitors of 2D6 and the one strong inhibitor of 2D6 would still render the phenotype poor. The total score for 2D6 would be 1.04 (0.67+0.36), still within the range of poor (see Table 4). Even if the phenotype for 2D6 was normal, the method of adjusting the phenotype of the present invention would predict a risk of adverse events with the combination of drugs in this example.

Figure 2:
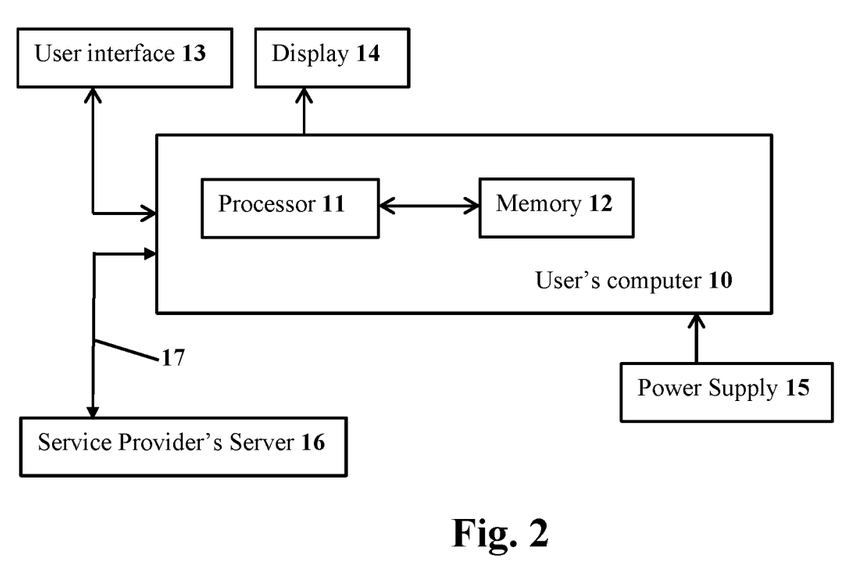
FIG. 2 is a diagram of a computer system that may be used to implement the method of the present invention.

This method of adjusting phenotypes can be implemented, in part, as a computer program in any standard computer/processor system well known in the art. A service provider can provide the software to implement the calculations of the method. FIG. 2, for example, illustrates a user's computer 10 having a processor 11, memory 12, a user interface 13, display 14, and a power supply 15. The computer 10 may be connected to a service provider's server 16 through the internet 17. All that is required is an entry by the user 11 into the computer 10 through interface 13 of the names of the drugs to be administered to a patient and the measured genotypes of the CYP450 drug metabolizing enzymes of the patient. The age of the patient can also be entered along with any other factors that affect drug metabolism. This information is transmitted to a service provider's server 16, for example, through the internet 17. Within seconds, adjusted phenotypes can be provided by the service provider's server 16 to the user's computer 10. The adjusted phenotypes can be retrieved from the user's computer 10 by methods well known in the art. The service provider's software and server 16 retrieve all the necessary data to make calculations of adjusted phenotypes for the user. A user can then use the adjusted phenotypes to quickly estimate the risk of an adverse drug event occurring with any of the drugs to be administered. The dosages of the drugs to be administered are then adjusted based on the risk assessment and administered to the patient.

This method of adjusting phenotypes uses databases that identify all medications influenced by CYP450 interactions. These databases include:

Elsevier elsevier.com/solution/clinical-pharmacology;
Elsevier Gold Standard: elsevier.com/promo/clinical-solutions/drug-information?;
PharmGKB: pharmgkb.org/;
CPIC Guidelines and Drug Bank: cpipgx.org/guidelines/;
Epocrates/Athena landing.athenahealth.com/epocrates-clincals?; and
PharmVAR pharmvar.org/.
The databases provide the CYP450 enzymes for which all the drugs are substrates and describe
for each drug whether the drug is a weak, moderate, or strong inducer or inhibitor of any CYP450 enzyme.

This method of adjusting phenotypes has been validated by analyzing and interpreting data from over 50,000 patients who received multiple drug therapy (polypharmacy) and who had pharmacogenetic testing for CYP450 genotypes. The values used herein to calculate adjusted phenotypes provide accurate CYP450 drug metabolizing enzyme phenotypes to make accurate risk assessment of adverse events occurring with multi-drug therapy. Because the method can be implemented in a computer adjusted phenotypes can be provided to a user quickly.

The foregoing description has been limited to specific embodiments of this invention. It will be apparent, however, that variations and modifications may be made by those skilled in the art to the disclosed embodiments of the invention, with the attainment of some or all of its advantages and without departing from the spirit and scope of the present invention. For example, the method can be used to determine if an alternate drug with less effects on drug metabolism can replace another drug. The method can be used for any drug metabolizing enzyme that has been identified and characterized with regard to drug metabolism. Scoring can be in any desired form as long as it reflects changes in phenotype. The method can be used for multiple drug dosing in non-human subjects, such as dogs, cats, farm animals, etc.

It will be understood that various changes in the details, materials, and methods which have been described above in order to explain the nature of this invention may be made by those skilled in the art without departing from the principle and scope of the invention as recited in the following claims.

The invention claimed is:

1. A computer-based method for adjusting patient phenotypes for multiple drugs and for reducing side effects from multiple drug dosing in a patient using the adjusted phenotypes, wherein the multiple drugs are inducers and/or inhibitors of CYP450 enzymes and wherein the patient has various disease states and is in need of treatment thereof with the multiple drugs, comprising:
   1) obtaining, by one or more users, tissue or fluid from a patient, analyzing the tissue or fluid, and obtaining CYP450 enzyme genotypes of the patient;
   2) entering, by the one or more users into the users' computer systems, names of the multiple drugs and the CYP450 enzyme genotypes of the patient, wherein a dose per drug label of each of the multiple drugs is known by the one or more users;
   3) converting, by the one or more users' computer systems, the CYP450 enzyme genotypes of the patient to standard baseline phenotypes using a table of standard baseline phenotypes programmed in the one or more users' computer systems;
   4) providing, by the one or more users' computer systems, a numerical score for each of the standard baseline phenotypes using a table of standard phenotype scores for baseline phenotypes programmed in the one or more users' computer systems;
   5) searching, by the one or more users' computer systems, one or more drug databases and identifying each of said multiple drugs that is an inducer or an inhibitor for each of the CYP450 enzymes;
   6) for each of the multiple drugs that is an inducer, adjusting by the one or more users' computer systems the standard baseline phenotype scores for the CYP450 enzymes which are induced using an inducer factor obtained from an inducer factor table programmed in the one or more users' computer systems, and for each of the multiple drugs that is an inhibitor, adjusting, by the one or more users' computer systems, the standard baseline phenotype scores for the CYP450 enzymes which are inhibited using an inhibitor factor obtained from an inhibitor factor table programmed in the users' computer systems, thereby obtaining an adjusted phenotype score for each of the CYP450 enzymes which are induced or inhibited;
   7) converting, by the one or more users' computer systems, the adjusted phenotype scores to adjusted phenotypes for each CYP450 enzyme which is induced or inhibited, using an adjusted phenotype look up table provided in the users' computer systems;
   8) displaying to the one or more users, by the one or more users' computer systems, adjusted phenotypes for each CYP450 enzyme which is induced or inhibited;
   9) determining by the one or more users the risk of occurrence of adverse events with the use of each of these multiple drugs based upon the displayed adjusted phenotype of each CYP450 enzyme for which each of the these multiple drugs is a substrate, adjusting, by the one or more users, the dose per drug label of each of the multiple drugs based upon the determination of risk of occurrence of adverse events with the use of each of the multiple drugs, and providing the adjusted dose of the dose per drug label of each of the multiple drugs; and
   10) receiving by the patient for each of the multiple drugs the adjusted dose of the dose per drug label, thereby minimizing the side effects of the multiple drug dosing in the patient.

2. The computer-based method of claim 1, wherein the table of standard baseline phenotypes has a range of phenotypes from poor to intermediate to normal to ultrarapid, wherein the standard baseline phenotype scores increase in amount negatively from normal to ultrarapid, and wherein the standard baseline phenotype scores increase in amount positively from normal to poor.

3. The computer-based method of claim 1 further comprising identifying by the one or more users' computer systems, whether each of said multiple drugs is a strong, medium, or weak inducer, or a strong, moderate, or weak inhibitor of each of the CYP450 enzymes.

4. The computer-based method of claim 2 further comprising for each drug that is an inducer, the inducer factor is a negative number, increasing in amount from a weak inducer to a strong inducer, and for each drug that is an inhibitor, the inhibitor factor is a positive number, increasing in amount from a weak inhibitor to a strong inhibitor.

5. The computer-based method of claim 2, wherein a positive number, programmed into the one or more users' computer systems, is added to all the standard baseline phenotype scores by the one or more users' computer systems in patients 65 years of age or older, wherein the patients' ages are entered into the one or more users' computer systems.

6. The computer-based method of claim 2, wherein all the standard baseline phenotype scores are adjusted by adding a positive number for doses greater than 115% of average starting dose, per drug label, and all the standard baseline phenotype scores are adjusted by adding a negative number for doses less than 85% of average daily dose, per drug label.

7. A computer-based method for adjusting patient phenotypes for multiple drugs and for reducing side effects from multiple drug dosing in a patient using the adjusted phenotypes, wherein the multiple drugs are inducers and/or inhibitors of CYP450 enzymes and the patient has various disease states and is in need of treatment thereof with the multiple drugs, comprising:
   1) obtaining, by one or more users, tissue or fluid from a patient, analyzing the tissue or fluid, and obtaining CYP450 enzyme genotypes of the patient;
   2) entering, by the one or more users into the one or more users' computer systems, names of the multiple drugs and the CYP450 enzyme genotypes of the patient, wherein a dose per drug label of each of the multiple drugs is known by the one or more users;
   3) converting, by the one or more users' computer systems, the CYP450 enzyme genotypes of the patient to standard baseline phenotypes using a table of standard baseline phenotypes provided in the software of the one or more users' computer systems;
   4) providing by the one or more users' computer systems, a numerical score for each of the standard baseline phenotypes using a table of scores for baseline phenotypes programmed in the one or more users' computer systems;

5) searching, by the one or more users' computer systems, one or more drug databases and identifying each of said multiple drugs that is an inducer or inhibitor of each of the CYP450 enzymes;

6) for each of the multiple drugs that is an inducer, adjusting by the one or more users' computer systems the standard baseline phenotype scores for the CYP450 enzymes which are induced using an inducer factor obtained from an inducer factor table programmed in the one or more users' computer systems, and for each of the multiple drugs that is an inhibitor, adjusting, by the one or more users' computer systems, the standard baseline phenotype scores for the CYP450 enzymes which are inhibited using an inhibitor factor obtained from an inhibitor factor table programmed in the one or more users' computer systems, thereby obtaining an adjusted phenotype score for each of the CYP450 enzymes which are induced or inhibited;

7) converting, by the one or more users' computer systems, the adjusted phenotype scores to adjusted phenotypes for each CYP450 enzyme which is induced or inhibited, using an adjusted phenotype look up table provided in the one or more users' computer systems;

8) displaying to the one or more users, by the one or more users' computer systems, adjusted phenotypes for each CYP450 enzyme which is induced or inhibited;

9) determining by the one or more users the risk of occurrence of adverse events with the use of each of these multiple drugs based upon the displayed adjusted phenotype of each CYP450 enzyme for which each of the these multiple drugs is a substrate, adjusting, by the one or more users, the dose per drug label of each of the multiple drugs based upon the determination of risk of occurrence of adverse events with the use of each of the multiple drugs, and providing the adjusted dose of the dose per drug label of each of the multiple drugs; and 10) receiving by the patient for each of the multiple drugs the adjusted dose of the dose per drug label, thereby minimizing the side effects of the multiple drug dosing in the patient, wherein the table of standard baseline phenotypes has a range of phenotypes from poor to intermediate to normal to ultrarapid, wherein the standard baseline phenotype scores increase in amount negatively from normal to ultrarapid, and wherein the standard baseline phenotype scores increase in amount positively from normal to poor; and 11) further comprising identifying, by the one or more users' computer systems, whether each of said multiple drugs is a strong, medium, or weak inducer, or a strong, moderate, or weak inhibitor of each of the CYP450 enzymes.

8. The computer-based method of claim 7 further comprising for each drug that is an inducer, the inducer factor is a negative number, increasing in amount from a weak inducer to a strong inducer, and for each drug that is an inhibitor, the inhibitor factor is a positive number, increasing in amount from a weak inhibitor to a strong inhibitor.

9. The computer-based method of claim 7, wherein a positive number, programmed into the one or more users' computer systems, is added to all the standard baseline phenotype scores by the one or more users' computer systems in patients 65 years of age or older, wherein the patients' ages are entered into the one or more users' computer systems.

10. The computer-based method of claim 7, wherein all the standard baseline phenotype scores are adjusted by adding a positive number for doses greater than 115% of average starting dose, per drug label, and the standard baseline phenotype scores are adjusted by adding a negative number for doses less than 85% of average daily dose, per drug label.

11. A computer-based method of treating a patient with multiple drugs, wherein the multiple drugs are inducers and/or inhibitors of CYP450 enzymes and the patient has various disease states and is in need of treatment thereof with the multiple drugs, comprising:

1) obtaining, by one or more users, tissue or fluid from a patient, analyzing the tissue or fluid, and obtaining CYP450 enzyme genotypes of the patient;

2) entering, by one or more users through one or more users' computer systems into a computer system of a service provider over a network, names of the multiple drugs and the CYP450 enzyme genotypes of the patient, wherein a dose per drug label of each of the multiple drugs is known by the one or more users;

3) converting, by the computer system of a service provider, the CYP450 enzyme genotypes of the patient to standard baseline phenotypes using a table of standard baseline phenotypes provided in the computer system of the service provider;

4) providing, by the computer system of the service provider, a numerical score for each of the standard baseline phenotypes using a table of standard phenotype scores for baseline phenotypes programmed in one or more users' computer systems;

5) searching by the computer system of the service provider one or more drug databases and identifying by the computer system of the service provider each of said multiple drugs that is an inducer or inhibitor of each of the CYP450 enzymes;

6) for each of the multiple drugs that is an inducer, adjusting by the computer system of the service provider the standard baseline phenotype scores for the CYP450 enzymes which are induced using an inducer factor obtained from an inducer factor table programmed in the computer system of the service provider, and for each of the multiple drugs that is an inhibitor, adjusting, by the computer system of the service provider, the standard baseline phenotype scores for the CYP450 enzymes which are inhibited using an inhibitor factor obtained from an inhibitor factor table programmed in the computer system of the service provider, thereby obtaining an adjusted phenotype score for each of the CYP450 enzymes which are induced or inhibited;

7) converting, by the computer system of the service provider, the adjusted phenotype scores to adjusted phenotypes for each CYP450 enzyme which is induced or inhibited, using an adjusted phenotype look up table provided in the computer system of the service provider;

8 displaying to the one or more users, by the one or more users' computer systems, adjusted phenotypes for each CYP450 enzyme which is induced or inhibited;

9) determining by the one or more users the risk of occurrence of adverse events with the use of each of these multiple drugs based upon the displayed adjusted phenotype of each CYP450 enzyme for which each of the these multiple drugs is a substrate, adjusting, by the one or more users, the dose per drug label of each of the multiple drugs based upon the determination of risk of occurrence of adverse events with the use of each of the multiple drugs, and providing the adjusted dose of the dose per drug label of each of the multiple drugs; and 10) receiving by the patient for each of the multiple drugs the adjusted dose of the dose per drug label, thereby minimizing the side effects of the multiple drug dosing in the patient.

12. The computer-based method of claim 11, wherein the table of standard baseline phenotypes has a range of phenotypes from poor to intermediate to normal to ultrarapid, and wherein the standard baseline phenotype scores increase in amount negatively from normal to ultrarapid, and wherein the standard baseline phenotype scores increase in amount positively from normal to poor.

13. The computer-based method of claim 11 further comprising identifying, by the computer system of the service provider, whether each of said multiple drugs is a strong, medium, or weak inducer, or a strong, moderate, or weak inhibitor of each of the CYP450 enzymes.

14. The computer-based method of claim 12, further comprising for each drug that is an inducer adding, by the of the computer system of the service provider, a negative number, increasing in amount from a weak inducer to a strong inducer, to the standard baseline phenotype scores for the CYP450 enzymes which are induced by said each drug, and for each drug that is an inhibitor adding, by the computer system of the service provider, a positive number, increasing in amount from a weak inhibitor to a strong inhibitor, to the standard baseline phenotype scores for the CYP450 enzymes which are inhibited by said each drug.

15. The computer-based method of claim 12, wherein a positive number, programmed in the computer system of the service provider, is added to all the standard baseline phenotype scores by the computer system of the service provider in patients 65 years of age or older, wherein the patients' ages are entered into the computer system of the service provider.

16. The computer-based method of claim 12, wherein all the standard baseline phenotype scores are adjusted by the computer system of the service provider by adding a positive number for doses greater than 115% of average starting dose, per drug label, and the standard baseline phenotype score is adjusted by the computer system of the service provider by adding a negative number for doses less than 85% of average daily dose, per drug label.

17. The computer-based method of claim 12 further comprising identifying, by the computer system of the service provider, whether each of said multiple drugs is a strong, medium, or weak inducer, or a strong, moderate, or weak inhibitor of each of the CYP450 enzymes.

18. The computer-based method of claim 11, further comprising for each drug that is an inducer adding, by the computer system of the service provider, a negative number, increasing in amount from a weak inducer to a strong inducer, to the standard baseline phenotype scores for the CYP450 enzymes which are induced, and for each drug that is an inhibitor adding, by the computer system of the service provider, a positive number, increasing in amount from a weak inhibitor to a strong inhibitor, to the standard baseline phenotype scores for the CYP450 enzymes which are inhibited by said each drug.

* * * * *